United States Patent
Bearss et al.

(10) Patent No.: US 8,759,384 B2
(45) Date of Patent: Jun. 24, 2014

(54) OXO-IMIDAZOLYL COMPOUNDS

(76) Inventors: David J. Bearss, Cedar Hills, UT (US); Hariprasad Vankayalapati, Draper, UT (US); Yong Xu, Midvale, UT (US); Charles Erec Stabbins, New York, NY (US); Vincent A. Fischetti, West Hempstead, NY (US)

( * ) Notice: Subject to any disclaimer, the term of this patent is extended or adjusted under 35 U.S.C. 154(b) by 583 days.

(21) Appl. No.: 12/454,062

(22) Filed: May 11, 2009

(65) Prior Publication Data
US 2009/0298900 A1    Dec. 3, 2009

Related U.S. Application Data

(60) Provisional application No. 61/127,494, filed on May 12, 2008.

(51) Int. Cl.
| A61K 31/415 | (2006.01) |
| C07D 233/00 | (2006.01) |
| C07D 405/06 | (2006.01) |
| C07D 409/06 | (2006.01) |
| A61K 31/4166 | (2006.01) |

(52) U.S. Cl.
CPC ............ *C07D 405/06* (2013.01); *C07D 409/06* (2013.01); *A61K 31/4166* (2013.01)
USPC ............. 514/389; 548/316.1; 548/315.4; 548/315.1; 548/311.1

(58) Field of Classification Search
CPC . C07D 405/06; C07D 409/06; A61K 31/4166
USPC .................. 548/311.1, 315.1, 315.4
See application file for complete search history.

(56) References Cited

U.S. PATENT DOCUMENTS

| 5,998,447 A | 12/1999 | Stilz et al. |
| 6,514,952 B1 | 2/2003 | Stilz et al. |
| 2002/0052396 A1 | 5/2002 | Bailey et al. |
| 2003/0195213 A1 | 10/2003 | Bailey et al. |
| 2004/0198741 A1 | 10/2004 | Bailey et al. |
| 2005/0042213 A1 | 2/2005 | Gelder et al. |
| 2010/0210577 A1* | 8/2010 | Singh et al. .............. 514/37 |

FOREIGN PATENT DOCUMENTS

| EP | 0237138 | 9/1987 |
| WO | WO-2005/016227 A2 | 2/2005 |
| WO | WO-2007/062078 A2 | 5/2007 |
| WO | WO 2008005651 | * 1/2008 |

OTHER PUBLICATIONS

Patani et al. "Bioisosterism: A rational Approach in Drug Design," Chem. Review, 1996, vol. 96, pp. 3147-3176.*
Leshcheva et al., Izvestiya Bysshikh Uchebnykh Zavedenii, Khimiya I Khimicheskaya Teckhnologiya (2003), 46(5), 105-108.
Pardasani et al., Phosphorus, Sulfur and Silicon and the Related Elements (2002), 177(10), 2435-2443.
Chazeau et al., European Journal of Medicinal Chemistry (1992), 27 (6),615-625.
Hill et al., J. Amer. Chem. Soc., (1924), 46, 2806-2810.

* cited by examiner

*Primary Examiner* — Shengjun Wang
(74) *Attorney, Agent, or Firm* — Shu Lee

(57) ABSTRACT

Compounds represented by Formula I and II, or pharmaceutically acceptable salts thereof:

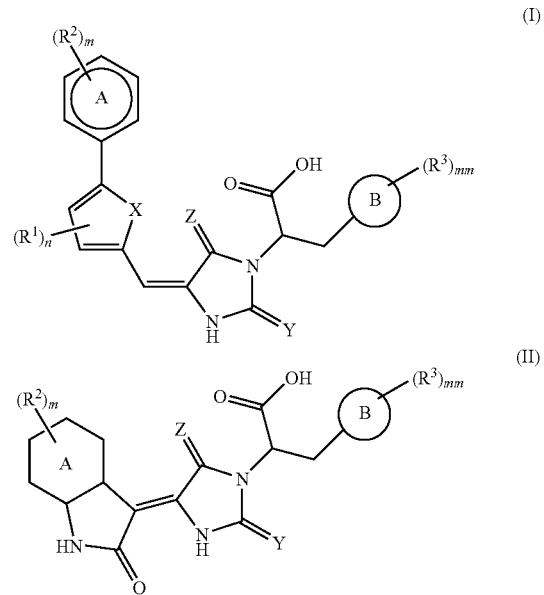

inhibit bacterial 2-epimerase and are useful anti-infective agents.

8 Claims, No Drawings

OXO-IMIDAZOLYL COMPOUNDS

This application claims the benefit of U.S. Patent Application No. 61/127,494 filed May 12, 2008.

BACKGROUND OF THE INVENTION

The present invention is directed to oxo-imidazolyl compounds. In particular, the present invention is directed to oxo-thioxo-imidazolyl compounds useful in the treatment of infectious diseases, including bacterial infections.

Bacterial infection remains a problem—particularly with each discovered new resistance to existing antibacterial drugs. Thus, there is a continuing need for new compounds that are useful in the treatment of infectious diseases, including bacterial infections.

There are 2-epimerase enzymes specific either to bacteria or animals that are not utilized by the other. For example, UDP-N-acetylglucosamine 2-epimerase is an important enzyme intermediary used in animal cellular amino sugar metabolism. UDP-N-acetylglucosamine 2-epimerase, however, is not found in bacteria. Instead, UDP-N-acylglucosamine 6-phosphate 2-epimerase is utilized by bacteria. We have identified compounds that inhibit gram-positive-bacteria-specific 2-epimerase enzymes. Accordingly, such compounds have use in disrupting the metabolism of gram positive bacteria without affecting host animals, including humans, that do not utilize the gram-positive-bacteria-specific 2-epimerase.

International Patent Publication No. WO 2007062078 describes the preparation of amide containing heterocyclic compounds as thrombopoietin activity modulators. International Patent Publication No. WO 2005016227 describes the screening for heparanase-activating proteinases for use in the therapeutic degradation of heparins. U.S. Patent Publication No. 2005042213 describes screening proteases participating in heparanase activation, and pharmaceutical compounds for medical uses. U.S. Patent Publication Nos. 2002052396, 2003195213, and 2004198741 describe rhodanine derivatives, preparation thereof, compositions, and methods for treating or preventing Flaviviridae family viral infections and associated diseases. U.S. Pat. Nos. 5,998,447 and 6,514,952 describe the preparation of 5-membered-ring heterocycles as inhibitors of leudocyte adhesion and VLA-4 antagonists.

E. V. Leshcheva et al., Izvestiya Bysshikh Uchebnykh Zavedenii, Khiimiya I Khimicheskaya Teckhnologiya (2003), 46(5), 105-108 describes new functional derivatives of 4,4,6-trimethyl-4H-pyrrolo[3,2,1-I,J]quinolin-1,2-diones. R. T. Pardasani et al., Phosphorus, Sulfur and Silicon and the Related Elements (2002), 177(10), 2435-2443 describes syntheses of indigold dye precursors and bioactive compounds via condensation of 1,2- and 1,4-diones with thiohydantoins. V. Chazeau et al., European Journal of Medicinal Chemistry (1992), 27(6),615-625 describes study of 5-arylidene-2-thiohydantoins with potential immunomodulating and anticancer activities. International Patent Publication No. EP 237138 describes the preparation of heterocyclylidenethiozolidine derivatives as aldose reductase inhibitors and pharmaceutical compositions containing them. M. K. Rout, J. Indian chemical Society (1958), 35, 287-293 describes thiohydantoin derivatives and their use in the estimation of silver, mercury, and copper. A. J. Hill et al., J. Amer. Chem. Soc., (1924), 46, 2806-2810 describes condensation reactions of cyclic ketones: the action of isatin and isatin α-chloride upon certain hydantoins.

SUMMARY OF THE INVENTION

The present invention is generally directed to compounds, and pharmaceutical compositions comprising said compounds, where the compounds have the following general structures (I) and (II) below:

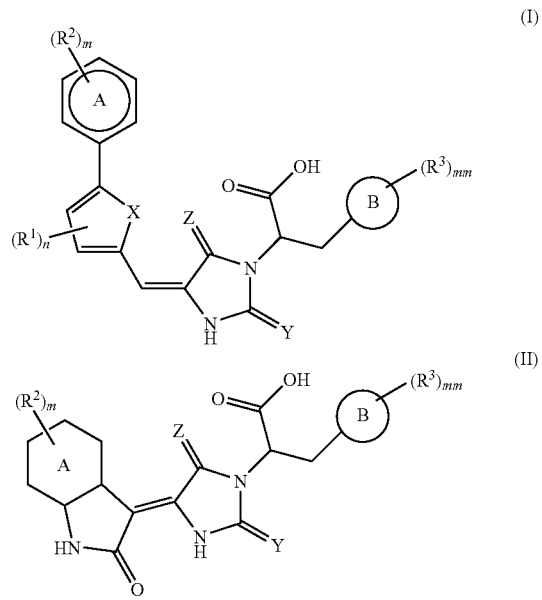

including stereoisomers, prodrugs and pharmaceutically acceptable salts thereof, wherein $R^1$, $R^2$, $R^3$, $R^4$ and X, Y, Z, A and B are defined herein.

These compounds of the present invention have utility over a broad range of therapeutic applications, and may be used to treat diseases, such as infection, that are mediated at least in part by bacterial 2-epimerase activity. Accordingly, in one aspect of the invention, the compounds described herein are formulated as pharmaceutically compositions for administration to a subject in need thereof.

In another aspect, the invention provides methods for treating or preventing infection, which method comprises administering to a patient in need of such a treatment and therapeutically effective amount of a compound described herein or a pharmaceutically acceptable composition comprising said compound.

Another aspect of the invention relates to inhibiting 2-epimerase activity in a biological sample, which method comprises containing the biological sample with a compound described herein, or a pharmaceutically acceptable composition comprising said compound.

Another aspect of this invention relates to a method of inhibiting bacterial 2-epimerase activity in a patient, which method comprises administering to the patient a compound described herein or a pharmaceutically acceptable composition comprising said compound.

The following compounds are known from various compound libraries:

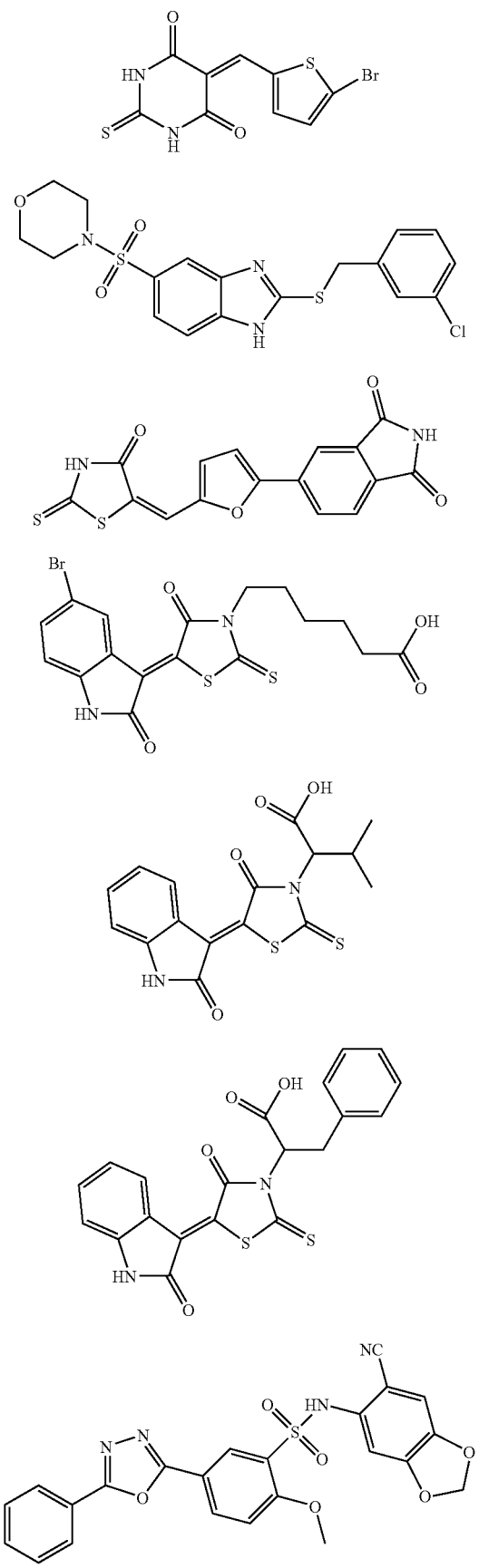
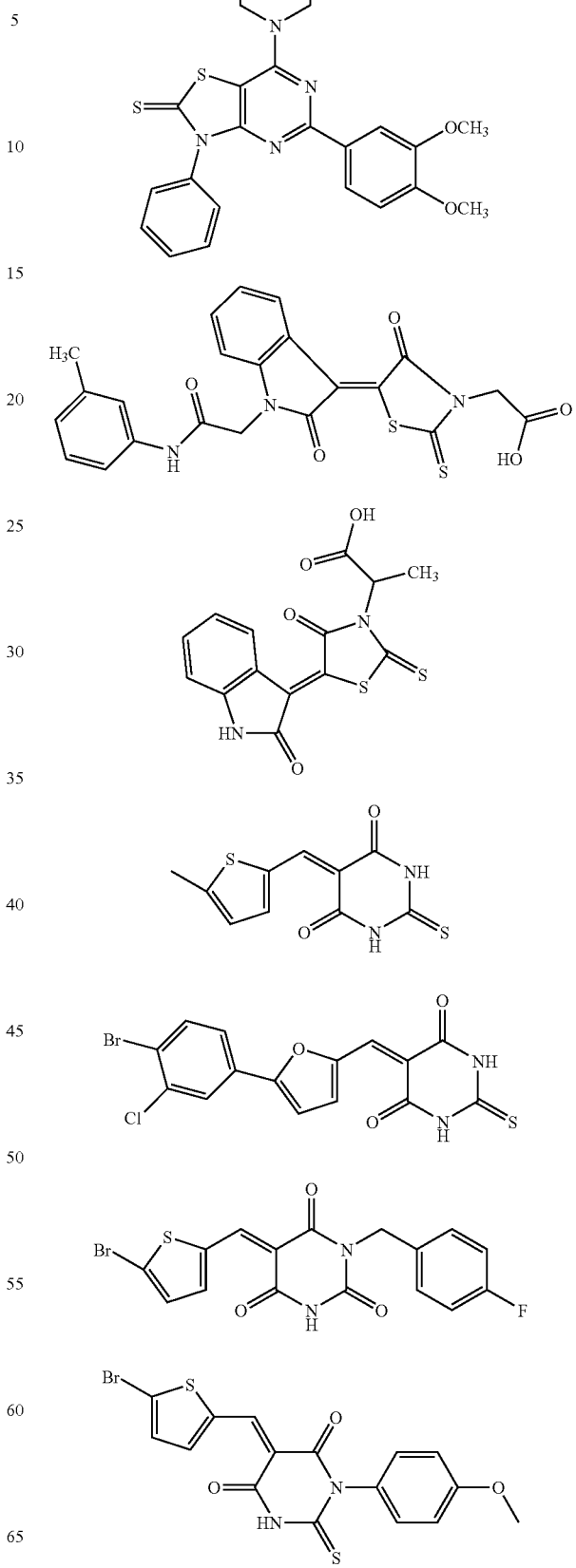

-continued
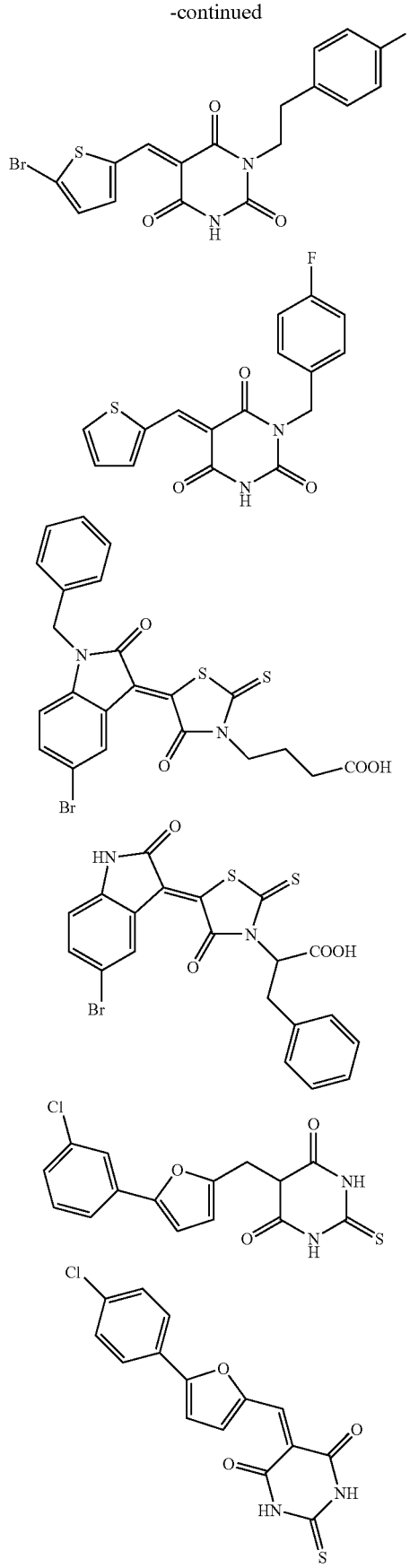
-continued
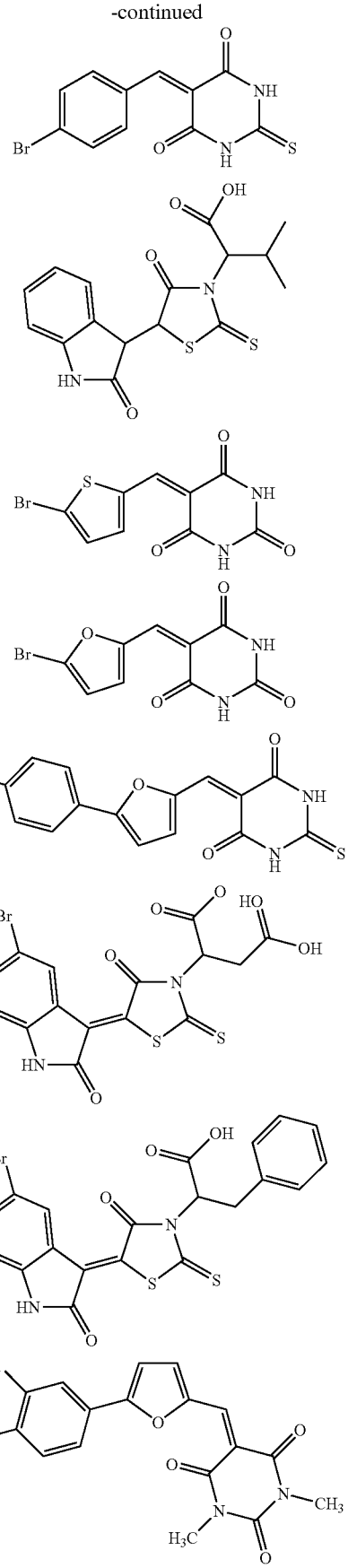

-continued

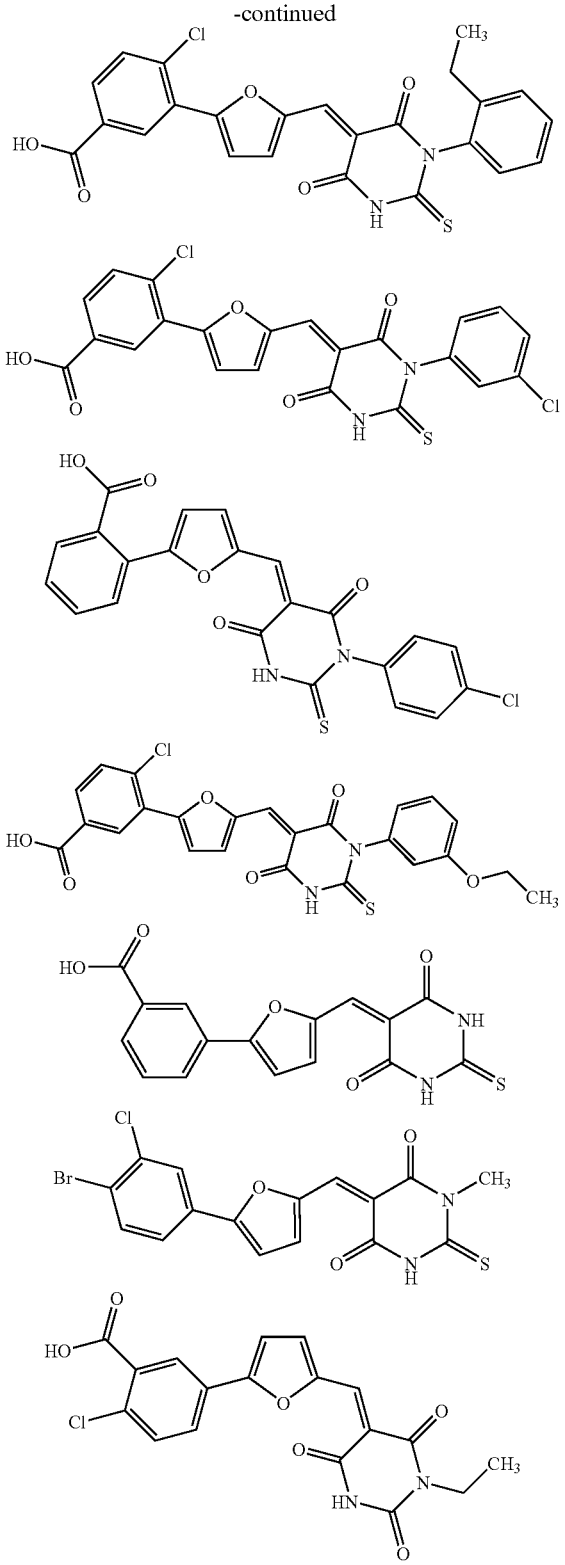

DETAILED DESCRIPTION OF THE INVENTION

As described above, there are 2-epimerase enzymes specific either to bacteria or animals that are not utilized by the other. For example, UDP-N-acetylglucosamine 2-epimerase is an important enzyme intermediary used in animal cellular amino sugar metabolism. UDP-N-acetylglucosamine 2-epimerase, however, is not found in bacteria. Instead, UDP-N-acylglucosamine 6-phosphate 2-epimerase is utilized by bacteria.

The non-hydrolyzing bacterial UDP-N-acetylglucosamine 2-epimerases (epimerase) catalyze the reversible conversion of UDP-N-acetylglucosamine (UDP-GlcNAc) into UDP-N-acetylmannosamine (UDP-ManNAc) (Kawamura et al., *J Biol Chem* 254(17):8457-8465 (1979) and Kawamura et al.,*J Biol Chem* 253(10):3595-3601 (1978)). The latter is an intermediate in the biosynthesis of several bacterial cell surface polysaccharides as well as the enterobacterial common antigen (ECA). The enterococcal common antigen is a surface-associated glycolipid common to all members of the enterobacteriacea family (Kuhn et al., *FEMS Microbiol Rev* 4(3): 195-222, 58-464 (1988)). The importance of UDP-GlcNAc 2-epimerase in the biosynthesis of polysaccharides in gram-positive bacteria is highlighted by the presence of two functionally redundant copies of these enzymes in species such as *Staphyloccocus aureus* and *Bacillus anthracis*. The bacterial epimerase is related to the bi-functional mammalian UDP-GlcNAc 2-epimerase/ManNAc kinase, a hydrolyzing enzyme that converts UDP-GlcNAc into UDP and ManAc and phosphorylates the latter into ManNAc 6-phosphate (Hinderlich et al., *J Biol Chem* 272(39):24313-24318 (1997)). The mammalian enzyme catalyzes the rate-limiting step in sialic acid biosynthesis and is a key regulator of cell surface sialylation in humans (Keppler et al., *Science* 284 (5418):1372-1376 (1999)).

A unique feature of the bacterial epimerases is their allosteric regulation by the substrate UDP-GlcNAc, which acts as an activator. In the absence of this activator, virtually no UDP-ManNAc is epimerized in the reverse reaction (Samuel et al., *Biochim Biophys Acta* 1700(1):85-91 (2004)), but when trace amounts of UDP-GlcNAc are added, the reaction proceeds to its normal equilibrium. This suggests that UDP-GlcNAc is required for the enzyme to acquire a conformation in which it is catalytically competent. This requirement is not found in the mammalian form of the enzyme.

The present invention is directed to a compound represented by Formula I:

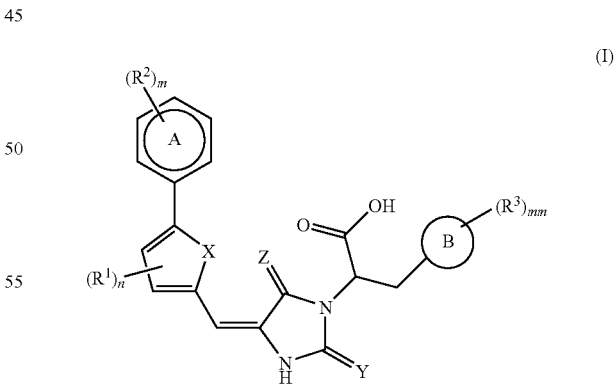

(I)

or a pharmaceutically acceptable salt thereof, wherein
X, Y, and Z each independently is O, S, or $NR^4$;
A is aryl or hetaryl; or A is halo;
B is single-ringed aryl, hetaryl, or hetcyclyl; or B is $CH_3$;
wherein A is halo and B is $CH_3$ cannot occur in same compound;
$R^1$ in each instance independently is $C_{0-4}$alkyl;

$R^2$ in each instance independently is $C_{0-4}$alkyl, $C_{1-4}$alkoxy, halo, —CF$_2$H, —CF$_3$, —OCF$_3$, —SCF$_3$, —SF$_5$;

$R^3$ in each instance independently is $C_{0-4}$alkyl;

$R^4$ in each instance independently is $C_{0-4}$alkyl, or a single-ringed aryl, hetaryl, or hetcyclyl;

n is 0, 1, or 2; and m and mm each independently is 0, 1, 2, 3, 4, or 5.

The present invention also is directed to a compound represented by Formula II:

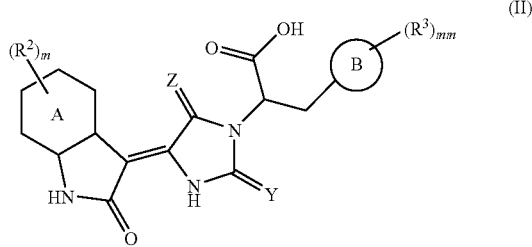

or a pharmaceutically acceptable salt thereof, wherein

Y, Z each independently is O, S, or NR$^4$;

A is aryl or hetaryl;

B is single-ringed aryl, hetaryl, or hetcyclyl;

$R^2$ in each instance independently is $C_{0-4}$alkyl, $C_{1-4}$alkoxy, halo, —CF$_2$H, —CF$_3$, —OCF$_3$, —SCF$_3$, —SF$_5$;

$R^3$ in each instance independently is $C_{0-4}$alkyl;

$R^4$ in each instance independently is $C_{0-4}$alkyl, or a single-ringed aryl, hetaryl, or hetcyclyl;

n is 0, 1, or 2; and m and mm each independently is 0, 1, 2, 3, 4, or 5.

In one aspect, the present invention is directed to a compound represented by Formula I, wherein Z is O, Y is S, and the other variables are as defined above for Formula I.

In an embodiment of this aspect, the present invention is directed to a compound represented by Formula I, wherein Z is O, Y is S, A is aryl, and the other variables are as defined above for Formula I.

In another embodiment of this aspect, the present invention is directed to a compound represented by Formula I, wherein Z is O, Y is S, B is aryl, and the other variables are as defined above for Formula I.

In yet another embodiment of this aspect, the present invention is directed to a compound represented by Formula I, wherein Z is O, Y is S, A is aryl, B is aryl, and the other variables are as defined above for Formula I.

In still another embodiment of this aspect, the present invention is directed to a compound represented by Formula I, wherein Z is O, Y is S, A is phenyl, B is phenyl, and the other variables are as defined above for Formula I.

In yet still another embodiment of this aspect, the present invention is directed to a compound represented by Formula I, wherein Z is O, Y is S, X is S, and the other variables are as defined above for Formula I.

In yet another embodiment of this aspect, the present invention is directed to a compound represented by Formula I, wherein Z is O, Y is S, X is S, A is aryl, B is aryl, and the other variables are as defined above for Formula I.

In another embodiment of this aspect, the present invention is directed to a compound represented by Formula I, wherein Z is O, Y is S, X is O, and the other variables are as defined above for Formula I.

In yet still another embodiment of this aspect, the present invention is directed to a compound represented by Formula I, wherein Z is O, Y is S, X is O, A is aryl, B is aryl, and the other variables are as defined above for Formula I.

In another aspect, the present invention is directed to a compound represented by Formula II, wherein Z is O, Y is S, and the other variables are as defined above for Formula II.

In an embodiment of this aspect, the present invention is directed to a compound represented by Formula II, wherein Z is O, Y is S, A is aryl, B is aryl, and the other variables are as defined above for Formula II.

In another embodiment of this aspect, the present invention is directed to a compound represented by Formula II, wherein Z is O, Y is S, A is phenyl, B is phenyl, and the other variables are as defined above for Formula II.

As used herein, "CC$_{0-4}$alkyl" is used to mean an alkyl having 0 to 4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

As used herein unless otherwise specified, "alkyl", "alkenyl", and "alkynyl" includes straight or branched configurations. Lower alkyls, alkenyls, and alkynyls have 16 carbons. Higher alkyls, alkenyls, and alkynyls have more than 6 carbons.

As used herein unless otherwise specified, the terms "aryl" and "ar" are well known to chemists and include, for example, phenyl and naphthyl. Phenyl, naphthyl, tolyl, and xylyl are preferred.

As used herein unless otherwise specified, the terms "hetaryl" or "heteroaryl" are well known to chemists and include, for example, pyridinyl.

As used herein unless otherwise specified, "hetcyclyl" (also known as "heterocyclyl") is well known to chemists and contains at least one N, S or O hetero-ring atom, and includes saturated, unsaturated, partially saturated, mono or polycyclic (unless specified as single-ringed) hetcyclic groups such as, for example, pyrrolyl, pyrrolinyl, imidazoylyl, pyrazolyl, pyridyl, pyrimidinyl, pyrazinyl, pyridazinyl, triazolyl, tetrazolyl, pyrrolidinyl, imidazolidinyl, piperidyl, piperazinyl, homopiperazinyl, indolyl, isoindolyl, indolizinyl, benzimidazolyl, quinolyl, isoquinolyl, imidazopyridyl, indazolyl, benzotriazolyl, tetrazolo-pyridazinyl, pyranyl, furyl, 1H-tetrahydropyranyl, tetrahydrofuranyl, thienyl, oxazolyl, isoxazolyl, oxadiazoyl, oxazolinyl, morpholinyl, benzofuranyl, benzoxazolyl, benzoxadiazolyl, thiazolyl, thiadiazolyl, thiazolidinyl, benzothiazolyl, benzothiadiazolyl, benzofuranyl, or benzodioxyl and the like.

As used herein unless otherwise specified, "halogen" is fluorine, chlorine, bromine or iodine.

The above Formulas I, and II are shown without a definitive stereochemistry at certain positions. The present invention includes all stereoisomers of Formulas I, and II and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I or II in combination with a pharmaceutically acceptable carrier.

Preferably, the composition is comprised of a pharmaceutically acceptable carrier and a non-toxic therapeutically effective amount of a compound of Formula I or II as described above (or a pharmaceutically acceptable salt or N-oxide thereof).

Moreover, within this preferred embodiment, the invention encompasses a pharmaceutical composition for the treatment of disease by the inhibition of bacterial 2-epimerase activity, comprising a pharmaceutically acceptable carrier and a non-toxic therapeutically effective amount of compound of Formula I or II as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfinuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention or used by the methods of the present invention comprise a compound represented by Formula I, or II (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula I, or II. The compounds of Formula I or II, or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula I or II or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5g of active agent, compounded with an appropriate and convenient amount of carrier material, which may vary from about 5 to about 95 percent of the total composition. Unit dosage forms will generally contain between from about 1 mg to about 2g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I or II of this invention, or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I or II, or pharmaceutically acceptable salts or N-oxides thereof, may also be prepared in powder or liquid concentrate form.

Generally, dosage levels on the order of from about 0.01 mg/kg to about 150 mg/kg of body weight per day are useful in the treatment of bacterially infected conditions, or alternatively about 0.5 mg to about 10g per patient per day. For example, bacterially infected patients may be effectively treated by the administration of from about 0.01 to 100 mg of the compound per kilogram of body weight per day, or alternatively about 0.5 mg to about 7 g per patient per day.

Similarly, infections from *Staphylococcus aureus*, *Staphylococcus aureus* (MRSA), *Staphylococcus epidermidis*, *Streptococcus pyogenes*, *Streptococcus pneumonia*, *Streptococcus agalactiae*, Group C *streptococcus*, Group G *streptococcus*, *Enterococcus faecalis*, *Enterococcus faecium*, *Bacillus anthracis*, *Bacillus cereus*, *Escherichia coli*, *Pseudomonas areuginosa*, *Neisseria meningitides*, or *Neisseria gonorrhoeae* may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other anti-infection therapeutic compounds. For example, antibiotics and antiviral agents can be advantageous co-agents with the compounds of the present invention. Accordingly, the present invention includes compositions comprising the compounds represented by Formula I or II, or a pharmaceutically acceptable salt or N-oxide thereof, and an antibiotic agent or an antiviral inhibiting agent. The amounts of each can be therapeutically effective alone—in which case the additive effects can overcome infections resistant to treatment by monotherapy. The amounts of any can also be subtherapeutic—to minimize adverse effects, particularly in sensitive patients.

Thus, the compositions of the present invention include a compound according to Formula I or II, or a pharmaceutically acceptable salt or N-oxide thereof, and an antiviral or antibiotic agent.

The compounds of the present invention, or pharmaceutically acceptable salts or N-oxides thereof, can also be effectively administered in conjunction with other therapeutic compounds, aside from anti-infective agents. For example, therapeutic agents effective to ameliorate adverse side-effects can be advantageous co-agents with the compounds of the present invention.

Representative EXAMPLES of the present invention are summarized in Table 1 below:

General Synthetic Method for FORMULA I:

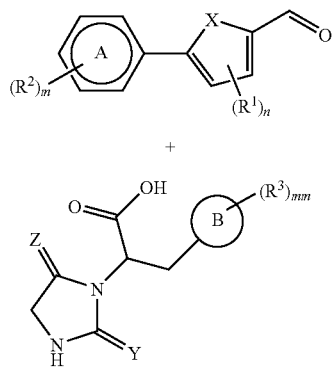
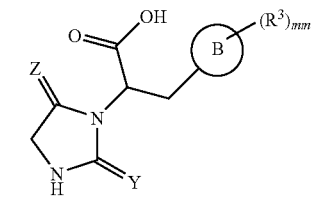

Scheme 1

To a mixture of oxo-thioxo-imidazolyl compound (1.0 eq.) and arylaldehyde (1.0 eq.) in acetic acid 5 mL is added β-alanine (2.69 mg, 0.030 mmol) and heat to 170° C. for 30 min under microwave irradiation. The resulting reaction mixture is cooled down and the solvent is removed. The pure product is obtained by column chromatography using MeOH/DCM, 2-7% ration solvent system.

General Synthetic Method for FORMULA II:

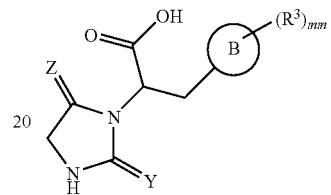

To a mixture of oxo-thioxo-imidazolyl compound (1.0 eq.) and indoline-2,3-dione (1.0 eq.) in acetic acid, 5 mL is added acetic anhydride 0.5 mL and heated to 80° C. for 2 h. The resulting reaction mixture is cooled down and the resulting reaction mixture is concentrated to dry. Purification by column chromatography using MeOH/DCM, 2-7% ration solvent system provided pure product as red solid.

TABLE 1

EXAMPLES:

| EX. | Formula/MW | Structure |
|---|---|---|
| 1 | $C_{20}H_{14}BrN_3O_4S$<br>MW: 472.31 | 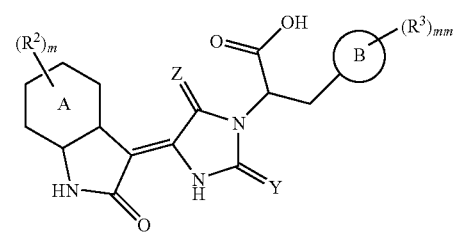 |

TABLE 1-continued

EXAMPLES:

| EX. | Formula/MW | Structure |
|-----|------------|-----------|
| 2 | $C_{20}H_{13}BrClN_3O_4S$<br>MW: 506.76 | 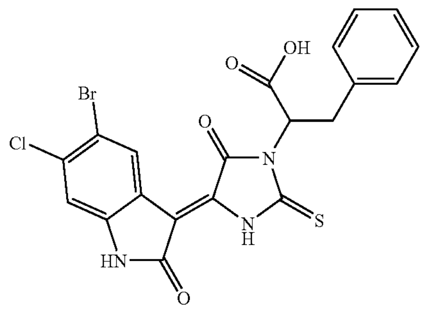 [SMILES: O=C1Nc2cc(Cl)c(Br)cc2/C1=C1/NC(=S)N(C(Cc2ccccc2)C(=O)O)C1=O] |
| 3 | $C_{23}H_{17}ClN_2O_3S_2$<br>MW: 468.04 | 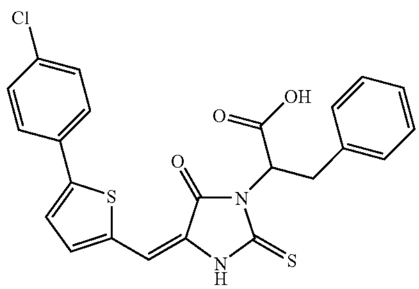 [SMILES: O=C(O)C(Cc1ccccc1)N1C(=O)/C(=C\c2ccc(-c3ccc(Cl)cc3)s2)NC1=S] |
| 4 | $C_{24}H_{20}N_2O_4S_2$<br>MW: 464.09 | 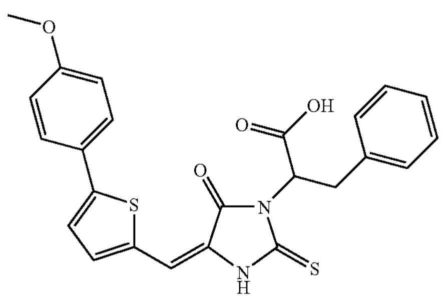 [SMILES: COc1ccc(-c2ccc(/C=C3/NC(=S)N(C(Cc4ccccc4)C(=O)O)C3=O)s2)cc1] |
| 5 | $C_{23}H_{17}ClN_2O_4S$<br>MW: 452.06 | 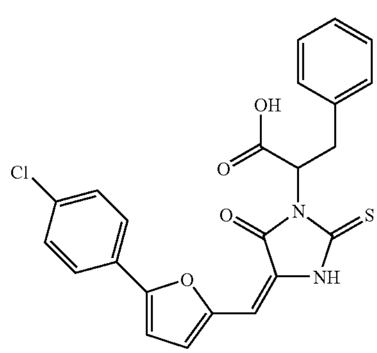 [SMILES: O=C(O)C(Cc1ccccc1)N1C(=O)/C(=C\c2ccc(-c3ccc(Cl)cc3)o2)NC1=S] |

TABLE 1-continued

EXAMPLES:

| EX. | Formula/MW | Structure |
|---|---|---|
| 6 | $C_{23}H_{16}Cl_2N_2O_4S$<br>MW: 487.06 | 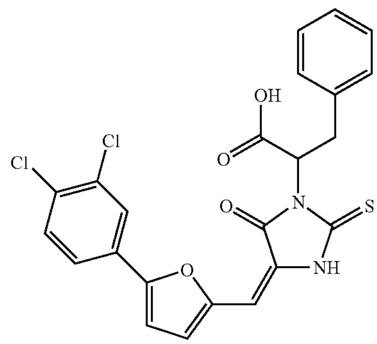 [SMILES: O=C(O)C(Cc1ccccc1)N1C(=O)/C(=C\c2ccc(-c3ccc(Cl)c(Cl)c3)o2)NC1=S] |
| 7 | $C_{23}H_{17}BrN_2O_3S_2$<br>MW: 511.99 | 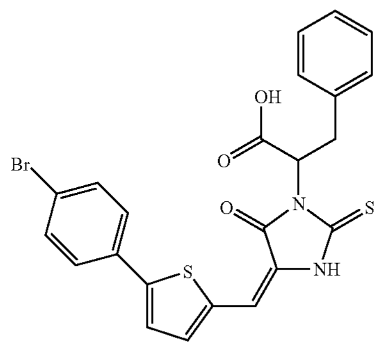 |
| 8 | $C_{23}H_{17}FN_2O_3S_2$<br>MW: 452.07 | 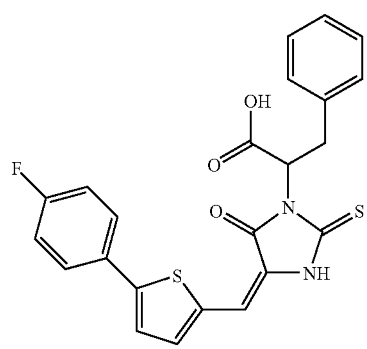 |
| 9 | $C_{23}H_{16}BrClN_2O_4S$<br>MW: 529.97 | 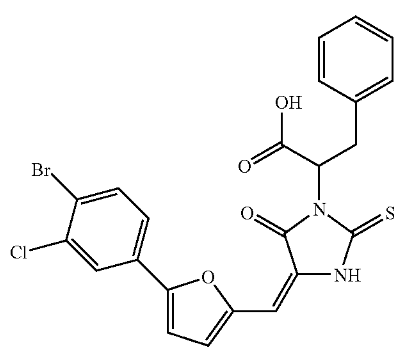 |

TABLE 1-continued

EXAMPLES:

| EX. | Formula/MW | Structure |
|-----|------------|-----------|
| 10 | C₂₃H₁₇BrN₂O₄S<br>MW: 497.36 | 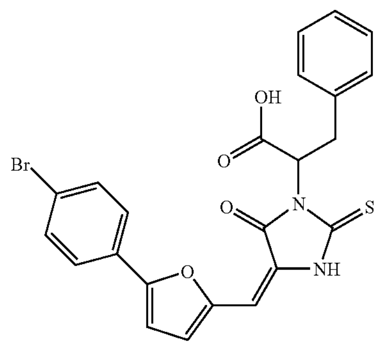 [SMILES: O=C(O)C(Cc1ccccc1)N1C(=O)/C(=C\c2ccc(-c3ccc(Br)cc3)o2)NC1=S] |
| 11 | C₂₃H₁₆BrClN₂O₃S₂<br>MW: 547.87 | 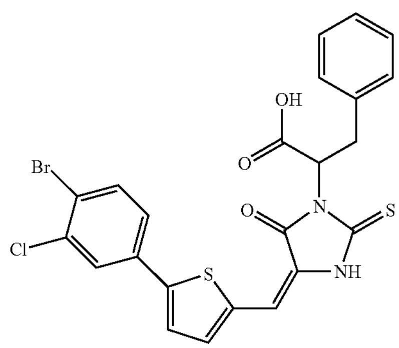 [SMILES: O=C(O)C(Cc1ccccc1)N1C(=O)/C(=C\c2ccc(-c3ccc(Br)c(Cl)c3)s2)NC1=S] |
| 12 | C₂₄H₁₇F₃N₂O₅S<br>MW: 502.46 | 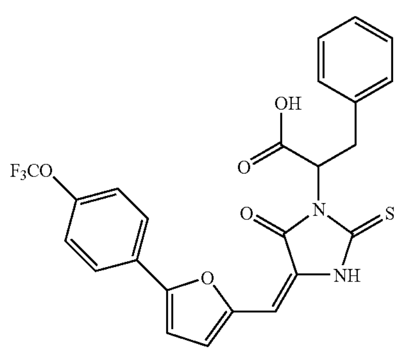 [SMILES: O=C(O)C(Cc1ccccc1)N1C(=O)/C(=C\c2ccc(-c3ccc(OC(F)(F)F)cc3)o2)NC1=S] |
| 13 | C₁₈H₁₄Cl₂N₂O₄S<br>MW: 425.29 | 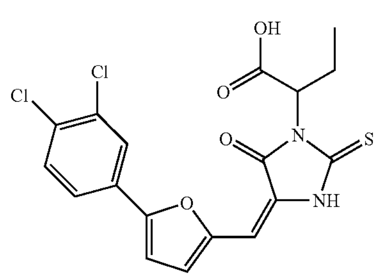 [SMILES: CCC(C(=O)O)N1C(=O)/C(=C\c2ccc(-c3ccc(Cl)c(Cl)c3)o2)NC1=S] |

TABLE 1-continued

EXAMPLES:

| EX. | Formula/MW | Structure |
|---|---|---|
| 14 | C$_{23}$H$_{17}$I$_1$N$_2$O$_4$S<br>MW: 544.36 | 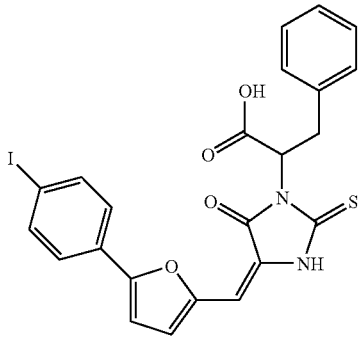 [SMILES: O=C(O)C(Cc1ccccc1)N1C(=O)/C(=C\c2ccc(-c3ccc(I)cc3)o2)NC1=S] |
| 15 | C$_{17}$H$_{13}$BrN$_2$O$_3$S$_2$<br>MW: 437.33 | 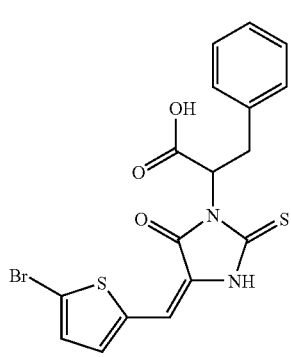 [SMILES: O=C(O)C(Cc1ccccc1)N1C(=O)/C(=C\c2ccc(Br)s2)NC1=S] |

TABLE 2

Inhibitive activity of SGI compounds on *Staphylococcus aureus* MRSA and *B. Anthracis*.

| Inhibitive activity | Conc. μM | EX. 1 | EX. 2 | EX. 3 | EX. 4 | EX. 5 | EX. 6 | EX. 7 |
|---|---|---|---|---|---|---|---|---|
| Anthracis | 30 | 88.02 | 98.76 | 100.00 | 100.00 | 99.71 | 96.71 | 96.71 |
|  | 10 | 2.50 | 40.22 | 100.00 | 0.00 | 68.90 | 99.55 | 97.71 |
|  | 3 |  | 11.29 | −5.40 | −3.85 | 4.99 | 96.18 | 67.90 |
| MRSA | 30 | −2.22 | 93.83 | 90.97 | 18.49 | 86.63 | 94.51 | 91.14 |
|  | 10 | −8.00 | −19.36 | −1.47 | −13.24 | −16.90 | 98.71 | 91.14 |
|  | 3 |  | −11.91 | −2.94 | −2.94 | −13.52 | −3.72 | −19.16 |

| Inhibitive activity | Conc. μM | EX. 8 | EX. 9 | EX. 10 | EX. 11 | EX. 12 | EX. 13 |
|---|---|---|---|---|---|---|---|
| Anthracis | 30 | 98.76 | 98.08 | 98.83 | 94.47 | 96.58 | 93.95 |
|  | 10 | 6.99 | 98.08 | 98.83 | 8.15 | 96.69 | 97.18 |
|  | 3 | 0 | 98.08 | 72.63 | 19.46 | 8.01 | 4.13 |
| MRSA | 30 | 46.21 | 95.65 | 95.36 | −0.89 | 95.15 | 92.90 |
|  | 10 | −24.79 | 95.65 | 92.50 | −7.45 | −6.26 | 4.53 |
|  | 3 | −15.78 | 17.90 | −9.55 |  | −1.32 | −2.47 |

Compounds of the claimed can be prepared by the condensation reaction (Knoevenagel reaction) of substituted thiohydantoins with corresponding aldehydes, ketones, or other reactive species. (Londhe, A.; et al., *Indian J. Heterocycl. Chem.* 2005, 15, 137-140.) The choice of reaction condition is crucial for the condensation reaction. The most frequently used basic condensation conditions are not workable for the preparation because the substituted thiohydantoin is basic liable and it decomposes immediately in basic media and elevated temperature. Therefore, we developed two kinds of reaction conditions which are suitable for substituted thiohydantoin condensation reaction. The starting material thiohydantoin is prepared by the cyclization reaction of efficient thiocarbonyl agent 1,1'-thiocarbonyldiimidazole with dipeptide Gly-DL-Phe. (Charton, J. et al., *Bioorg. Med. Chem. Lett.* 2005, 15, 4833-4837.) The first method is using acetate anhydride as promoter and the condensation reaction process readily at 80° C. for 2 h. (Hui, Y.-H. et al., *Youji Huaxue* 2006, 26, 391-395) The second method is using β-alanine as catalyst, which is a neutral amine acid, and the condensation reaction provided good yield in 30 min under microwave irradiation. (Prout, F. S. et al., *J. Org. Chem.* 1953, 18, 928-33).

EXAMPLES

Example 1

2-(4-(5-Bromo-2-oxoindolin-3-ylidene)-5-oxo-2-thioxoimidazolidin-1-yl)-3-phenylpropanoic acid, SGI-4003

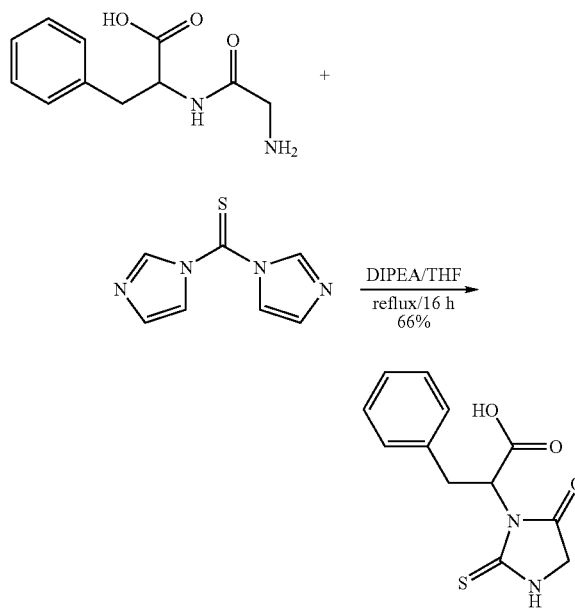

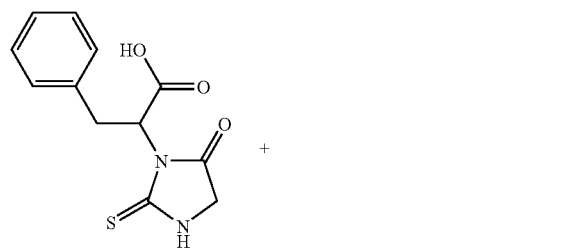

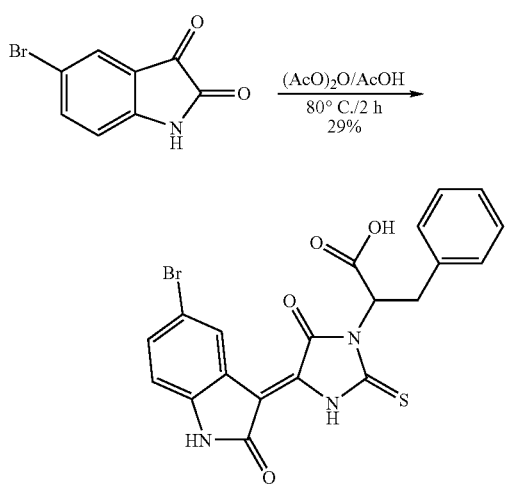

EX. 1

Synthesis of 2-(5-oxo-2-thioxoimidazolidin-1-yl)-3-phenylpropanoic acid

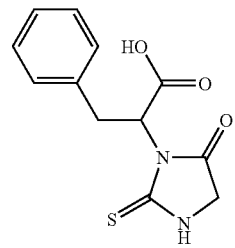 [SMILES: O=C(O)C(Cc1ccccc1)N1C(=O)CNC1=S]

To a mixture of Gly-DL-Phe (1.0 g, 4.50 mmol) and DIPEA (2.61 g, 20.25 mmol) in anhydrous THF 20 mL is added 1,1'-thiocarbonyldiimidazole (1.203 g, 6.75 mmol) and heated to reflux overnight. The resulting reaction mixture is concentrated to dry and the pure product (0.85 g, 3.22 mmol, yellow solid) is obtained by column chromatography using acetic acid/DCM, 0-5% ration solvent system. Spectral Data: $^1$H-NMR (CD$_3$OD/300 MHz): 6.45 (m, 5H), 4.80 (dd, J=11.7, 5.4 Hz, 1H), 3.15 (s, 2H), 2.87 (dd, J=13.8, 11.4 Hz, 1H), 2.70 (dd, J=14.4, 5.4 Hz, 1H). MS (ES+, m/z): 265.0 (M$^+$+1, 70.0).

To a mixture of 2-(5-oxo-2-thioxoimidazolidin-1-yl)-3-phenylpropanoic acid (0.130 g, 0.492 mol) and 5-bromoindoline-2,3-dione (00.101 g, 0.447 mmol) in acetic acid 5 mL is added acetic anhydride 0.5 mL and heated to 80° C. for 2 h. The resulting reaction mixture is cooled down and the resulting reaction mixture is concentrated to dry. After purification by column chromatography using MeOH/DCM, 2-7% ration solvent system, pure product as red solid EXAMPLE 1 (0.062 g, 0.131 mmol) is obtained. Spectral Data: $^1$H-NMR (CD$_3$OD/300 MHz): 8.71 (d, J=2.0 Hz, 1H), 7.39 (dd, J=8.4, 2.0 Hz, 1H), 7.20 (m, 5H), 6.80 (d, J=8.4 Hz, 1H), 5.64 (dd, J=11.6, 5.6 Hz, 1H), 3.61 (m, J=14.4, 5.4 Hz, 2H). MS (ES+, m/z): 472.0 (M$^+$, 100.0).

Example 2

2-(4-(5-Bromo-6-chloro-2-oxoindolin-3-ylidene)-5-oxo-2-thioxoimidazolidin-1-yl)-3-phenylpropanoic acid

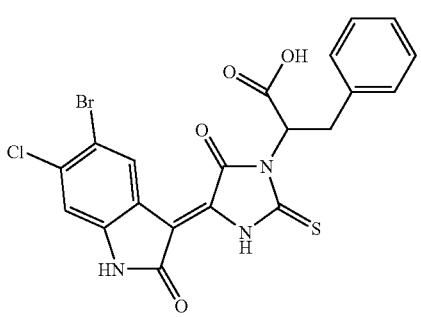 [SMILES: O=C1Nc2cc(Cl)c(Br)cc2/C1=C1/NC(=S)N(C(Cc2ccccc2)C(=O)O)C1=O]

To a mixture of 2-(5-oxo-2-thioxoimidazolidin-1-yl)-3-phenylpropanoic acid (0.200 g, 0.757 mmol) and 5-bromo-6-chloro-indoline-2,3-dione (0.179 g, 0.688 mmol) in acetic acid 5 mL is added acetic anhydride 0.5 mL and heated to 80° C. for 2 h. The resulting reaction mixture is cooled down and the resulting reaction mixture is concentrated to dry. After purification by column chromatography using MeOH/DCM, 2-7% ration solvent system, pure product as red solid EX. 2 (0.109 g, 0.109 mmol) is obtained. Spectral Data: $^1$H-NMR (CD$_3$OD/300 MHz): 8.94 (d, J=13.2 Hz, 1H), 7.15 (m, 6H), 5.54 (m, 1H), 3.53 (m, 2H). MS (ES+, m/z): 508.0 (M$^+$, 80.0).

Example 3

2-(4-((5-(4-Chlorophenyl)thiophen-2-yl)methylene)-5-oxo-2-thioxoimidazolidin-1-yl)-3-phenylpropanoic acid

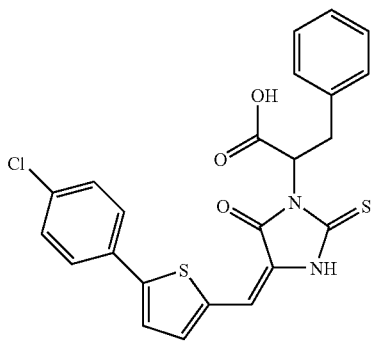 [SMILES: O=C(O)C(Cc1ccccc1)N1C(=O)/C(=C\c2ccc(-c3ccc(Cl)cc3)o2)NC1=S]

To a mixture of 2-(5-oxo-2-thioxoimidazolidin-1-yl)-3-phenylpropanoic acid (0.080 g, 0.304 mmol) and 5-(4-chorophenyl)thiophene-2-carbaldehyde (0.068 g, 0.304 mmol) in acetic acid 5 mL is added β-alanine (2.7 mg, 0.030 mmol) and heat to 170° C. for 30 min under microwave irradiation. The resulting reaction mixture is cooled down and the solvent is removed. The pure product (0.110 g, 0.235 mmol, red solid) is obtained by column chromatography using MeOH/DCM, 2-7% ration solvent system. $^1$H-NMR (CD$_3$OD/300 MHz): 7.66 (dd, J=8.7, 1.5 Hz, 2H), 7.50 (dm, J=12.6 Hz, 2H), 7.40 (d, J=8.4 Hz, 2H), 7.18 (m, 5H), 6.69 (s, 1H), 5.65 (dd, J=12.0, 4.5 Hz, 1H), 3.68 (dd, J=13.8, 12.0 Hz, 1H), 3.51 (dd, J=14.4, 4.5 Hz, 1H). MS (ES+, m/z): 469.5 (M$^+$+1, 30.0).

Example 4

2-(4-((5-(4-Methoxyphenyl)thiophen-2-yl)methylene)-5-oxo-2-thioxoimidazolidin-1-yl)-3-phenylpropanoic acid

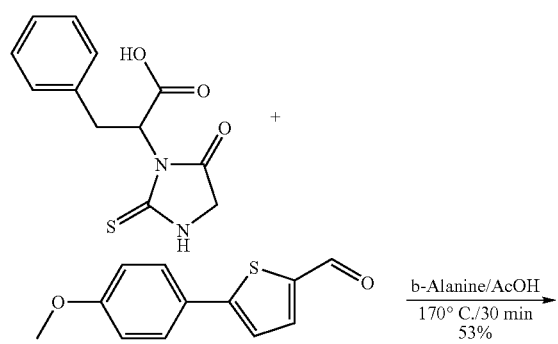

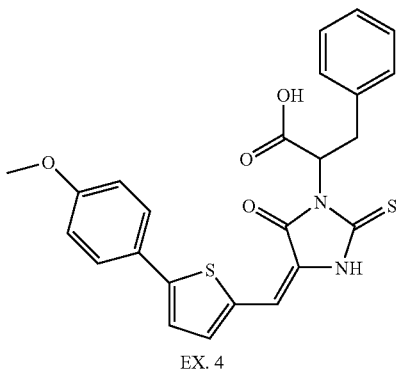

EX. 4

To a mixture of 2-(5-oxo-2-thioxoimidazolidin-1-yl)-3-phenylpropanoic acid (0.080 g, 0.303 mmol) and 5-(4-methoxyphenyl)thiophene-2-carbaldehyde (0.066 g, 0.303 mmol) in acetic acid 5 mL is added β-alanine (2.69 mg, 0.030 mmol) and heat to 170° C. for 30 min under microwave irradiation. The resulting reaction mixture is cooled down and the solvent is removed. The pure product (0.075 g, 0.162 mmol, red solid) is obtained by column chromatography using MeOH/DCM, 2-7% ration solvent system. $^1$H-NMR (CD3OD/300 MHz): 7.62 (m, 2H), 7.45 (m, 1H), 7.33 (m, 5H), 7.27 (d, J=13.2 Hz, 1H), 6.94 (d, J=6.9 Hz, 2H), 6.70 (s, 1H), 5.50 (m, 1H), 3.82 (s, 3H), 3.53 (m, 2H). MS (ES+, m/z): 465.1 (M++1, 20.0).

Example 5

2-(4-((5-(4-Chlorophenyl)furan-2-yl)methylene)-5-oxo-2-thioxoimidazolidin-1-yl)-3-phenylpropanoic acid

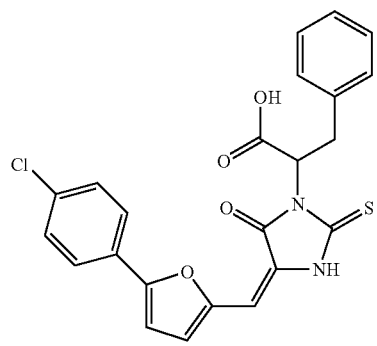

To a mixture of 2-(5-oxo-2-thioxoimidazolidin-1-yl)-3-phenylpropanoic acid (0.080 g, 0.304 mmol) and 5-(4-chorophenyl)thiophene-2-carbaldehyde (0.063 g, 0.304 mmol) in acetic acid 5 mL is added β-alanine (2.7 mg, 0.030 mmol) and heat to 170° C. for 30 min under microwave irradiation. The resulting reaction mixture is cooled down and the solvent is removed. The pure product (0.038 g, 0.084 mmol, red solid) is obtained by column chromatography using MeOH/DCM, 2-7% ration solvent system. $^1$H-NMR (CD$_3$OD/300 MHz): 7.81 (dm, J=9.0 Hz, 2H), 7.41 (dm, J=9.3 Hz, 2H), 7.14 (m, 5H), 6.98 (s, 2H), 6.42 (s, 1H), 5.51

(d, J=8.7 Hz, 1H), 3.75 (dd, J=11.7, 11.0 Hz, 1H), 3.55 (dd, J=15.3, 3.9 Hz, 1H). MS (ES⁻, m/z): 451.1 (M⁻−1, 100.0).

Example 6

2-(4-((5-(3,4-Dichlorophenyl)furan-2-yl)methylene)-5-oxo-2-thioxoimidazolidin-1-yl)-3-phenylpropanoic acid

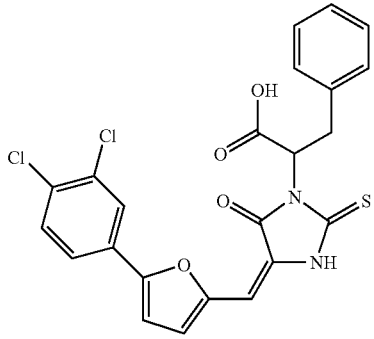 [SMILES: O=C(O)C(Cc1ccccc1)N1C(=O)/C(=C\c2ccc(-c3ccc(Cl)c(Cl)c3)o2)NC1=S]

To a mixture of 2-(5-oxo-2-thioxoimidazolidin-1-yl)-3-phenylpropanoic acid (0.055 g, 0.207 mmol) and 5-(3,4-dichloro-phenyl)thiophene-2-carbaldehyde (0.050 g, 0.207 mmol) in acetic acid 5 mL is added β-alanine (1.8 mg, 0.021 mmol) and heat to 170° C. for 30 min under microwave irradiation. The resulting reaction mixture is cooled down and the solvent is removed. The pure product (0.060 g, 0.123 mmol, red solid) is obtained by column chromatography using MeOH/DCM, 2-7% ration solvent system. ¹H-NMR (CDCl₃/CD₃OD/300 MHz): 7.84 (d, J=2.1 Hz, 1H), 7.60 (dd, J=8.7, 2.4 Hz, 1H), 7.44 (d, J=2.7 Hz, 1H), 7.17 (m, 6H), 6.85 (m, 1H), 6.42 (s, 1H), 5.61 (dd, J=11.1, 5.4 Hz, 1H), 3.66 (m, 1H), 3.53 (m, 1H). MS (ES⁻, m/z): 585.3 (M⁻, 100.0).

Example 6E (E)-2-(4-((5-(3,4-dichlorophenyl)furan-2-yl)methylene)-5-oxo-2-thioxoimidazolidin-1-yl)-3-phenylpropanoic acid To a mixture of 2-(5-oxo-2-thioxoimidazolidin-1-yl)-3-phenylpropanoic acid (0.110g, 0.416 mmol) and 5-(3,4-dichloro-phenyl)thiophene-2-carbaldehyde (0.100 g, 0.416 mmol) in acetic acid 10 mL is added β-alanine (1.8 mg, 0.021 mmol) and heat to 80° C. for 16 h. The resulting reaction mixture is cooled down and the solvent is removed. The pure product (0.070 g, 0.144 mmol, red solid) is obtained by column chromatography using MeOH/DCM, 2-7% ration solvent system. The product is further purified by recryatallization in hexane and DCM mixture and got pure E-isomer. ¹H-NMR (CDCl₃/CD₃OD/300 MHz): 7.84 (d, J=2.1 Hz, 1H), 7.60 (dd, J=8.7, 2.4 Hz, 1H), 7.44 (d, J=2.7 Hz, 1H), 7.17 (m, 6H), 6.85 (m, 1H), 6.42 (s, 1H), 5.61 (dd, J=11.1, 5.4 Hz, 1H), 3.66 (dd, J=14.1, 12.6 Hz, 1H), 3.53 (dd, J=14.1, 5.1 Hz, 1H). MS (ES⁻, m/z): 585.3 (M⁻, 100.0).

Example 7

2-(4-((5-(4-Bromophenyl)thiophen-2-yl)methylene)-5-oxo-2-thioxoimidazolidin-1-yl)-3-phenylpropanoic acid

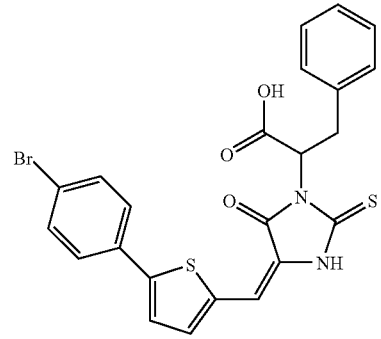

To a mixture of 2-(5-oxo-2-thioxoimidazolidin-1-yl)-3-phenylpropanoic acid (0.100 g, 0.378 mmol) and 5-(4-bromophenyl)thiophene-2-carbaldehyde (0.101 g, 0.378 mmol) in acetic acid 5 mL is added β-alanine (3.37 mg, 0.038 mmol) and heat to 170° C. for 30 min under microwave irradiation. The resulting reaction mixture is cooled down and the solvent is removed. The pure product (0.120 g, 0.234 mmol, red solid) is obtained by column chromatography using MeOH/DCM, 2-7% ration solvent system. ¹H-NMR (CD₃OD/300 MHz): 7.84 (m, 1H), 7.63 (m, 1H), 7.50 (m, 3H), 7.15 (m, 6H), 6.69 (s, 1H), 5.66 (dd, J=11.4, 5.1 Hz, 1H), 3.69 (dd, J=14.4, 12.0 Hz, 1H), 3.51 (dd, J=10.5, 5.1 Hz, 1H). MS (ES+, m/z): 511.3 (M⁻−1, 100.0).

Example 8

2-(4-((5-(4-Fluorophenyl)thiophen-2-yl)methylene)-5-oxo-2-thioxoimidazolidin-1-yl)-3-phenylpropanoic acid

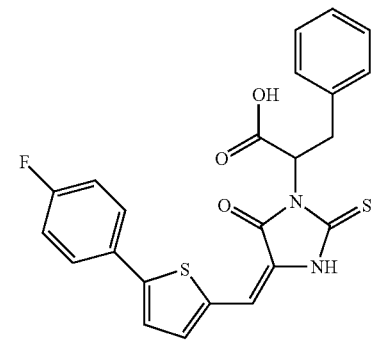

To a mixture of 2-(5-oxo-2-thioxoimidazolidin-1-yl)-3-phenylpropanoic acid (0.100g, 0.378 mmol) and 5-(4-fluorophenyl)thiophene-2-carbaldehyde (0.078 g, 0.378 mmol) in acetic acid 5 mL is added β-alanine (3.37 mg, 0.038 mmol) and heat to 170° C. for 30 min under microwave irradiation. The resulting reaction mixture is cooled down and the solvent is removed. The pure product (0.125 g, 0.276 mmol, red solid) is obtained by column chromatography using MeOH/DCM, 2-7% ration solvent system. ¹H-NMR (CD₃OD/300 MHz): 7.71 (m, 2H), 7.52 (d, J=4.5 Hz, 1H), 7.43 (d, J=4.5 Hz, 1H), 7.16 (m, 7H), 6.69 (s, 1H), 5.66 (dd, J=11.4, 5.1 Hz, 1H), 3.69 (dd, J=14.4, 11.7 Hz, 1H), 3.51 (dd, J=10.5, 5.1 Hz, 1H). MS (ES⁻, m/z): 451.4 (M⁻−1, 45.0).

Example 9

(E)-2-(4-((5-(4-bromo-3-chlorophenyl)furan-2-yl)methylene)-5-oxo-2-thioxoimidazolidin-1-yl)-3-phenylpropanoic acid

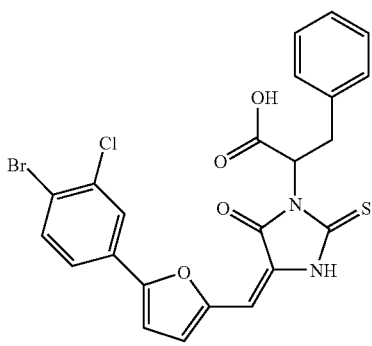 [SMILES: O=C(O)C(Cc1ccccc1)N1C(=O)/C(=C\c2ccc(-c3ccc(Br)c(Cl)c3)o2)NC1=S]

To a mixture of 2-(5-oxo-2-thioxoimidazolidin-1-yl)-3-phenylpropanoic acid (0.045 g, 0.175 mmol) and 5-(4-bromo-3-chloro-phenyl)thiophene-2-carbaldehyde (0.050 g, 0.175 mmol) in acetic acid 5 mL is added β-alanine (1.6 mg, 0.018 mmol) and heat to 170° C. for 30 min under microwave irradiation. The resulting reaction mixture is cooled down and the solvent is removed. The pure product (0.075 g, 0.141 mmol, red solid) is obtained by column chromatography using MeOH/DCM, 2-7% ration solvent system.

Example 10

(E)-2-(4-((5-(4-bromophenyl)furan-2-yl)methylene)-5-oxo-2-thioxoimidazolidin-1-yl)-3-phenylpropanoic acid

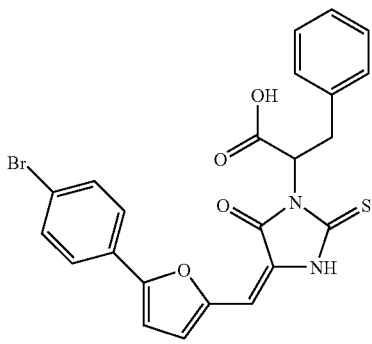

To a mixture of 2-(5-oxo-2-thioxoimidazolidin-1-yl)-3-phenylpropanoic acid (0.053 g, 0.199 mmol) and 5-(4-bromophenyl)thiophene-2-carbaldehyde (0.050 g, 0.199 mmol) in acetic acid 5 mL is added β-alanine (1.8 mg, 0.020 mmol) and heat to 170° C. for 30 min under microwave irradiation. The resulting reaction mixture is cooled down and the solvent is removed. The pure product (0.060 g, 0.120 mmol, red solid) is obtained by column chromatography using MeOH/DCM, 2-7% ration solvent system. ¹H-NMR (CD₃OD/300 MHz): 7.83 (dm, J=9.0 Hz, 2H), 7.44 (dm, J=9.3 Hz, 2H), 7.17 (m, 5H), 7.03 (s, 2H), 6.47 (s, 1H), 5.64 (d, J=8.7 Hz, 1H), 3.69 (m, 1H), 3.49 (m, 1H). MS (ES⁻, m/z): 495.2 (M⁻, 80.0).

Example 11

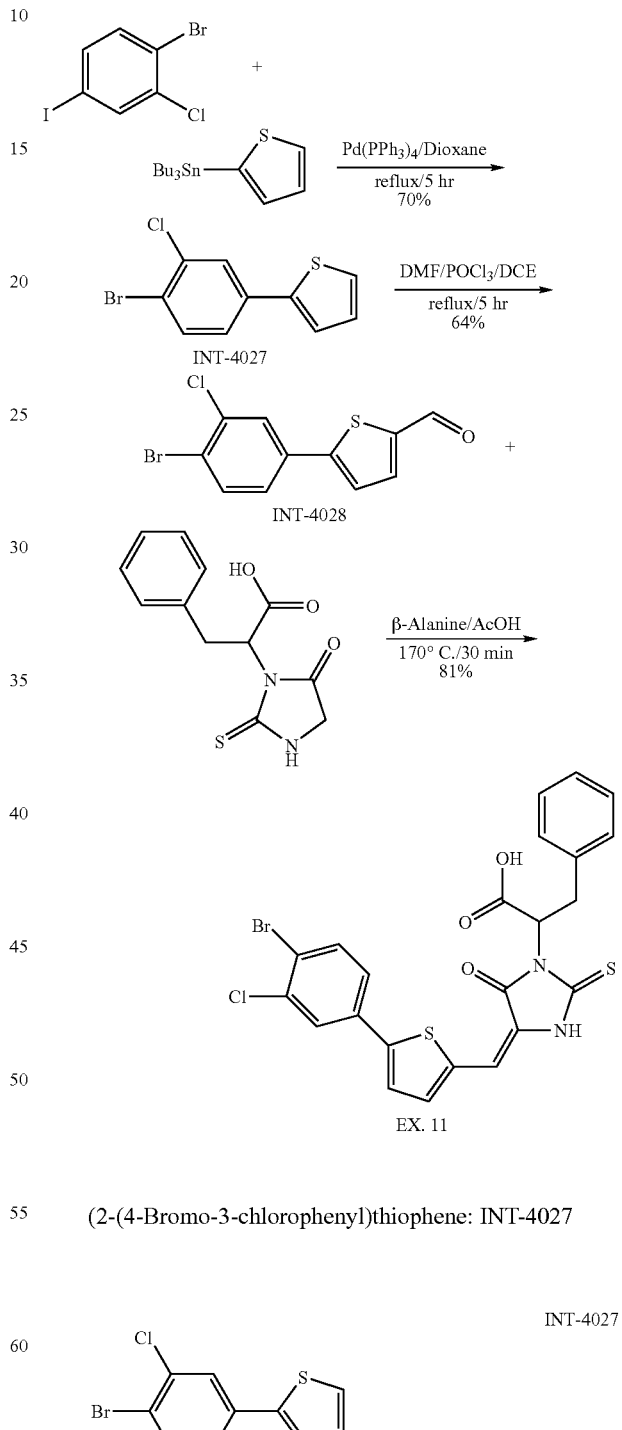

(2-(4-Bromo-3-chlorophenyl)thiophene: INT-4027

To a mixture of 1-bromo-2-chloro-4-iodobenzene (2.0 g, 6.30 mmol) in dioxane 30 mL, 2-tributylstannyl thiophene (2.352 g, 6.30 mmol), and 5% equivalent of Pd(PPh$_3$)$_4$ (0.364 g, 0.3155 mmol) is refluxed under nitrogen for 5 h. After cooling and evaporation of the solvent, the residue is dissolved in EtOAc 50 mL. 10% KF 30 mL is added and the solution is stirred at r.t. for 30 min. The resultant precipitate is removed by filtration. The solution is washed with water 20 mL×3, and dried with Na$_2$SO$_4$ and concentrated. The pure product (1.2 g, 4.39 mmol, white solid) is obtained by column chromatography using EtOAc/Hexane, 1-3% ration solvent system. $^1$H-NMR (CDCl$_3$/300 MHz): 7.74 (d, J=2.1 Hz, 1H), 7.65 (d, J=7.2 Hz, 1H), 7.37 (m, 3H), 7.14 (m, 1H). MS (ES$^-$, m/z): 529.2 (M$^+$−Br, 20.0).

2-(4-bromo-3-chlorophenyl)thiophene: INT-4028

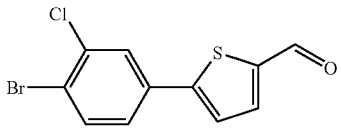

INT-4028

To a solution of DMF 1.2 mL and 1,2-dichloroethane 5 mL is slowly added a solution of POCl$_3$ (0.68 mL, 7.3 mmol) in 1,2-dichloroethane 5 mL with stirring over 20 min at 0-5° C. To the reaction mixture is slowly added a solution of INT-4027 (1.0 g, 3.66 mmol) in 1,2-dichloroethane 5 mL over 10 min below 10° C., and the mixture is stirred under reflux for 17 h. The resulting solution is poured into chilled 50% KOH (10 mL) and extracted with ethyl acetate. The extract is washed successively with 5% HCl, water, and brine, and dried over MgSO$_4$. The ethyl acetate solution is evaporated under reduced pressure to give a residue, which is purified by column chromatography using EtOAc/Hexane, 1-3% ration solvent system. The pure product (0.710 g, 2.35 mmol, white solid) is obtained. $^1$H-NMR (CDCl$_3$/300 MHz): 9.96 (s, 1H), 7.81 (d, J=2.7 Hz, 2H), 7.73 (d, J=8.4 Hz, 1H), 7.46 (m, 2H). MS (ES$^-$, m/z): 301.1 (M$^+$+1, 20.0).

(E)-2-(4-((5-(4-bromo-3-chlorophenyl)thiophen-2-yl)methylene)-5-oxo-2-thioxoimidazolidin-1-yl)-3-phenylpropanoic acid, EXAMPLE 11

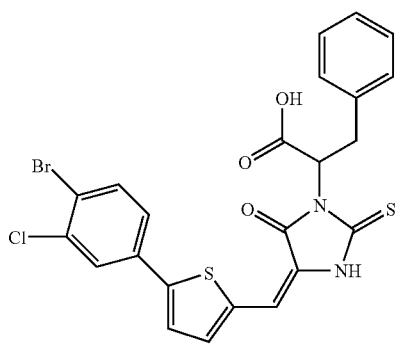

EX. 11

To a mixture of 2-(5-oxo-2-thioxoimidazolidin-1-yl)-3-phenylpropanoic acid (0.044 g, 0.175 mmol) and 5-(4-bromo-3-chloro-phenyl)thiophene-2-carbaldehyde (0.050 g, 0.166 mmol) in acetic acid 5 mL is added β-alanine (1.6 mg, 0.01 r8 mmol) and heat to 170° C. for 30 min under microwave irradiation. The resulting reaction mixture is cooled down and the solvent is removed. The pure product (0.075 g, 0.141 mmol, red solid) is obtained by column chromatography using MeOH/DCM, 2-7% ration solvent system. $^1$H-NMR (CDCl$_3$/300 MHz): 9.88 (br, 1H), 8.92 (br, 1H), 7.65 (m, 2H), 7.31 (m, 8H), 6.85 (s, 1H), 5.76 (dd, J=11.1, 5.4 Hz, 1H), 3.70 (m, 2H). MS (ES$^-$, m/z): 545.2 (M$^-$, 100.0).

Example 12

2-(4-((5-(4-Trifluoromethoxyphenyl)thiophen-2-yl)methylene)-5-oxo-2-thioxoimidazolidin-1-yl)-3-phenylpropanoic acid

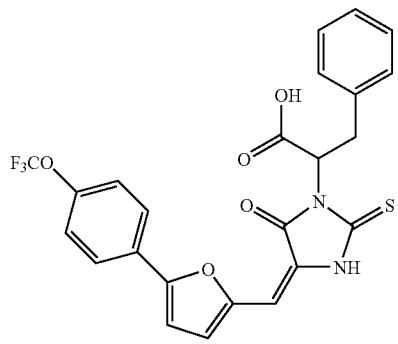 [SMILES: O=C(O)C(Cc1ccccc1)N1C(=O)/C(=C\c2ccc(-c3ccc(OC(F)(F)F)cc3)o2)NC1=S]

To a mixture of 2-(5-oxo-2-thioxoimidazolidin-1-yl)-3-phenylpropanoic acid (0.031 g, 0.117 mmol) and 5-(4-trifluoromethoxy-phenyl)thiophene-2-carbaldehyde (0.030 g, 0.117 mmol) in acetic acid 5 mL is added β-alanine (1.042 mg, 0.012 mmol) and heat to 170° C. for 30 min under microwave irradiation. The resulting reaction mixture is cooled down and the solvent is removed. The pure product (0.035 g, 0.069 mmol, red solid) is obtained by column chromatography using MeOH/DCM, 2-7% ration solvent system. $^1$H-NMR (CD$_3$OD/300 MHz): 7.91 (m, 2H), 7.32 (d, J=9.0 Hz, 2H), 7.14 (m, 5H), 7.02 (m, 2H), 6.47 (s, 1H), 5.64 (dd, J=11.1, 5.4 Hz, 11H), 3.70 (dd, J=14.1, 12.6 Hz, 1H), 3.53 (dd, J=14.1, 5.1 Hz, 1H). MS (ES$^-$, m/z): 501.4 (M$^-$, 100.0).

Example 13

2-(4-((5-(3,4-Dichlorophenyl)furan-2-yl)methylene)-5-oxo-2-thioxoimidazolidin-1-yl)butanoic acid

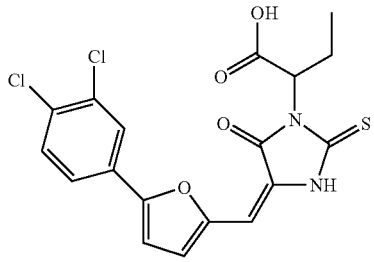 [SMILES: CCC(C(=O)O)N1C(=O)/C(=C\c2ccc(-c3ccc(Cl)c(Cl)c3)o2)NC1=S]

To a mixture of 2-(2-aminoacetamido)butanoic acid (0.5 g, 3.12 mmol) and DIPEA (1.812 g, 14.05 mmol) in anhydrous THF 10 mL is added 1,1'-thiocarbonyldiimidazole (0.834 g, 4.68 mmol) and heated to reflux overnight. The resulting reaction mixture is concentrated to dry and the pure product 2-(5-oxo-2-thioxoimidazolidin-1-yl)butanoic acid (0.24 g, 1.187 mmol, yellow solid) is obtained by column chromatography using acetic acid/DCM, 0-5% ration solvent system. $^1$H-NMR (CD$_3$OD/300 MHz): 5.21 (dd, J=10.5, 5.1 Hz, 1H), 4.09 (d, J=5.4 Hz, 2H), 2.25 (m, 2H), 0.90 (t, J=7.2 Hz, 3H). MS (ES+, m/z): 200.9 (M$^-$, 100.0).

To a mixture of 2-(5-oxo-2-thioxoimidazolidin-1-yl)butanoic acid (0.130 g, 0.643 mmol) and 5-(3,4-dichloro-phenyl)thiophene-2-carbaldehyde (0.155 g, 0.643 mmol) in acetic acid 5 mL is added β-alanine (5.72 mg, 0.064 mmol) and heat to 170° C. for 30 min under microwave irradiation. The resulting reaction mixture is cooled down and the solvent is removed. The pure product (0.060 g, 0.141 mmol, red solid) is obtained by column chromatography using MeOH/DCM, 2-7% ration solvent system. $^1$H-NMR (CD$_3$OD/300 MHz): 7.97 (d, J=2.1 Hz, 1H), 7.68 (dd, J=8.4, 2.1 Hz, 1H), 7.49 (d, J=4.8 Hz, 1H), 7.02 (m, 2H), 6.48 (s, 1H), 5.31 (dd, J=11.1, 5.4 Hz, 1H), 2.32 (m, 2H), 0.93 (t, J=7.2 Hz, 3H). MS (ES$^-$, m/z): 423.3 (M$^-$, 100.0).

Example 14

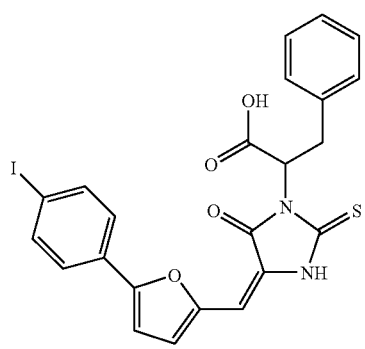 [SMILES: O=C(O)C(Cc1ccccc1)N1C(=O)/C(=C\c2ccc(-c3ccc(I)cc3)o2)NC1=S]

To a mixture of 2-(5-oxo-2-thioxoimidazolidin-1-yl)-3-phenylpropanoic acid (0.050 g, 0.189 mmol) and 5-(4-iodophenyl)thiophene-2-carbaldehyde (0.059 g, 0.189 mmol) in acetic acid 5 mL is added β-alanine (1.68 mg, 0.019 mmol) and heat to 170° C. for 30 min under microwave irradiation. The resulting reaction mixture is cooled down and the solvent is removed. The pure product (0.085 g, 0.125 mmol, red solid) is obtained by column chromatography using MeOH/DCM, 2-7% ration solvent system. $^1$H-NMR (CD$_3$OD/300 MHz): 7.72 (m, 2H), 7.49 (m, J=9.0 Hz, 2H), 7.18 (m, 5H), 7.89 (m, 2H), 6.45 (s, 1H), 5.62 (dd, J=11.1, 5.4 Hz, 1H), 3.69 (dd, J=14.1, 12.6 Hz, 1H), 3.53 (dd, J=14.1, 5.1 Hz, 1H). MS (ES$^-$, m/z): 560.0 (M$^-$, 100.0).

Fischetti Lab Protocol for Epimerase Inhibitor Growth Curves

All compounds are solubilized at a stock concentration of 5 mM in DMSO. They are sonicated in a sonicating water bath for 2 bursts of 10 s in order to break up the clumps. All compounds are treated similarly, regardless of clumping state, to ensure proper solubilization. Some compounds are sonicated more if necessary.

Since 3% DMSO is tolerable for most Gram+strains, that is the concentration used in our assay. Therefore, stock inhibitor compounds are diluted 1:5 (1 mM), 1:15 (0.3333 mM), and 1:50 (0.1 mM). Upon addition of [6 μL inhibitor+95 μL BHI] followed by+100 μL cells (at the beginning of the growth assay), the final concentrations become 30 μM, 10 μM, and 3 μM.

Currently, two strains are used for each growth assay: *B. anthracis* ΔSterne, and *Staphylococcus aureus* MRSA. Cells are inoculated from a single colony and then grown overnight for 16 h in BHI shaking at 150 rpm at 30° C. These are inoculated 1:100 into 25 mL BHI in a 125 mL flask, and grown for 3.5 h under the same conditions.

OD$_{600}$ of the exponential culture is then normalized to 0.220, and 100 μL of this is added to each well containing 100 μL [6 μL epimerase inhibitor compounds or DMSO alone+95 μL BHI]. A typical 96-well plate layout is used. The plate is inserted into a SpectraMax 96-well plate reader set at 25° C. The OD$_{600}$ is measured every 2 min with 40 s of shaking in between readings. The assay is monitored in this manner for 16 h, but sometimes for up to 20 h. Data is collected with SoftMaxPro software, and exported to Microsoft Excel for analysis.

The cells reach stationary phase typically at 40,000 s, so data is assessed at this point. The kinetic reading can help identify aberrations in the data (cell clumping, bubbles, etc.). The final results are expressed as % inhibition. This is achieved after subtracting the media background from all points, and then determining the percent of growth inhibition using this formula:

% Inhibition=100×(1-(OD$_{600}$ of inhibitor test curve at X seconds–OD$_{600}$ of media background)/(OD$_{600}$ of DMSO only control curve at X seconds–OD$_{600}$ of media background).

We claim:
1. A compound represented by Formula I:

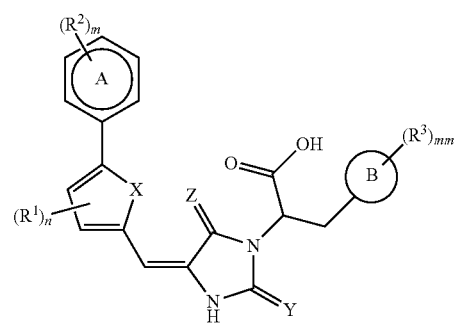

(I)

or a pharmaceutically acceptable salt thereof, wherein
X is O or S;
Y is S;
Z is O;
A is phenyl;
B is phenyl; or A is phenyl and B is CH$_3$; or A is bromo and B is phenyl;
(R$^1$)$_n$ is H;
R$^2$ in each instance independently is halo, methoxy, or OCF$_3$;
R$^3$ is H;
R$^4$ in each instance independently is C$_{0-4}$ alkyl, or a single-ringed aryl, hetaryl, or hetcyclyl; and
m is 1 or 2 and mm is 0.
2. The compound according to claim 1, wherein X is S.
3. The compound according to claim 1, wherein X is O.
4. The compound according to claim 1, wherein X is O, A is phenyl, and B is phenyl.
5. The compound according to claim 1 selected from the group consisting of

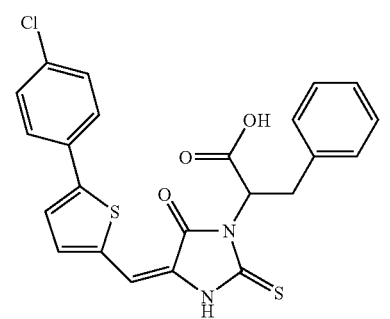
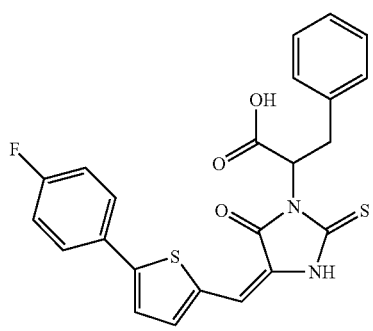
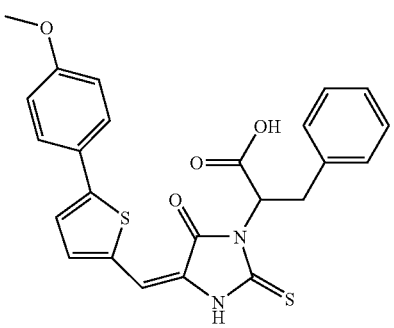
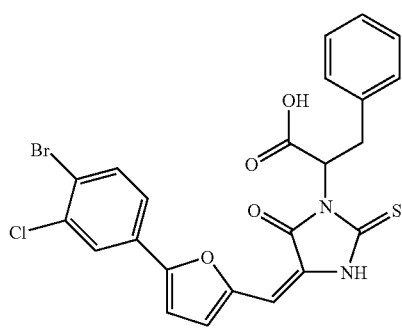
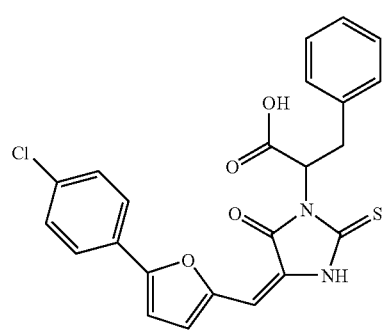
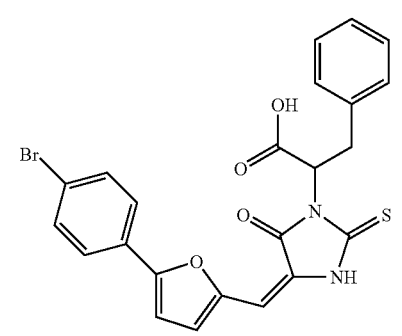
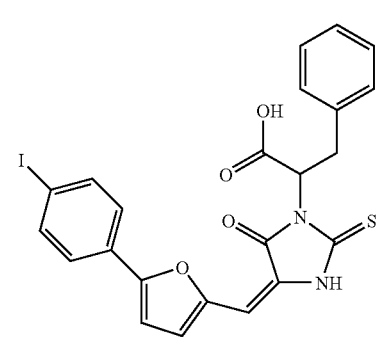
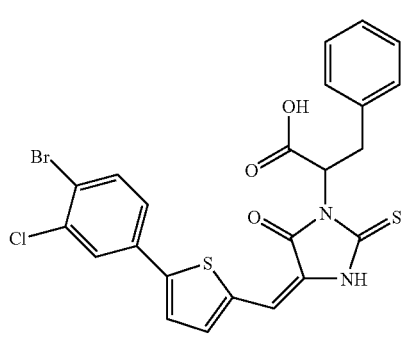
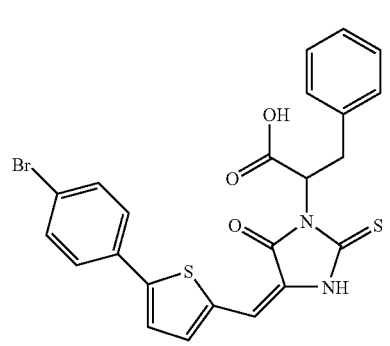
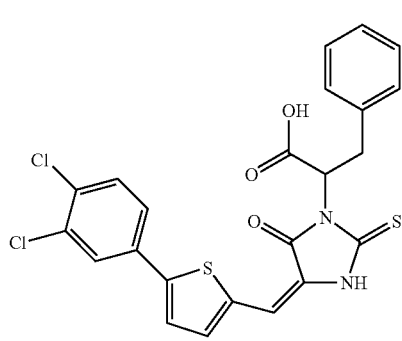 [SMILES: O=C(O)C(Cc1ccccc1)N1C(=O)/C(=C\c2ccc(-c3ccc(OC(F)(F)F)cc3)o2)NC1=S]

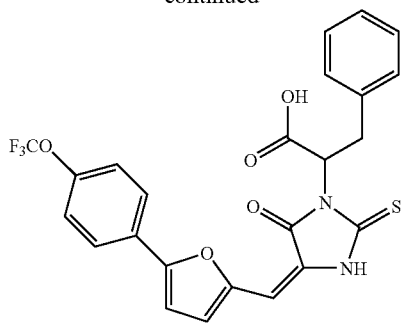

or a pharmaceutically acceptable salt thereof.

6. The compound according to claim 1 consisting of

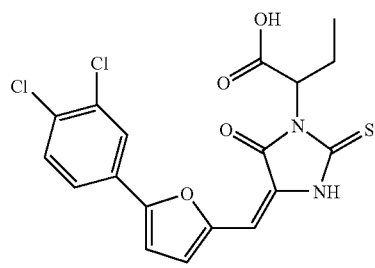

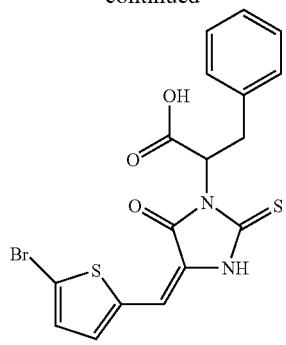

or a pharmaceutically acceptable salt thereof.

7. A composition comprising a compound according to claim 1 and a pharmaceutically acceptable excipient.

8. A method for treating infections from *Staphylococcus aureus, Staphylococcus aureus* (MRSA), *Staphylococcus epidermidis, Streptococcus pyogenes, Streptococcus pneumonia, Streptococcus agalactiae*, Group C *streptococcus*, Group G *streptococcus, Enterococcus jaecalis, Enterococcus jaecium, Bacillus anthracis, Bacillus cereus, Escherichia coli, Pseudomonas areuginosa, Neisseria meningitides*, or *Neisseria gonorrhoeae* comprising administering to a subject in need thereof a therapeutically effective amount of a compound according to claim 1.

* * * * *